United States Patent [19]

Vincent et al.

[11] 4,319,996

[45] Mar. 16, 1982

[54] FILTER WITH INITIALLY FLAT MEMBRANE AND CURVED MEMBRANE SUPPORT

[75] Inventors: Monty E. Vincent; Karlis Vizulis, both of Ann Arbor, Mich.

[73] Assignee: Gelman Sciences, Inc., Ann Arbor, Mich.

[21] Appl. No.: 205,229

[22] Filed: Nov. 10, 1980

[51] Int. Cl.³ ............................................. B01D 33/00
[52] U.S. Cl. .................................. 210/188; 210/398; 210/436; 210/472; 210/477
[58] Field of Search ................... 55/158, 159; 210/188, 210/247, 321, 349, 359, 398, 433.2, 433 M, 436, 445, 446, 455, 456, 472, 477, 482, 541, 927, 507–509

[56] References Cited

U.S. PATENT DOCUMENTS 3,520,416  7/1970  Keedwell .................. 210/508 X
4,157,967  6/1979  Meyst et al. .............. 210/927 X Primary Examiner—Charles N. Hart
Assistant Examiner—David R. Sadowski
Attorney, Agent, or Firm—Reising, Ethington, Barnard, Perry & Brooks

[57] ABSTRACT

The filter device of this invention comprises a housing with an inlet chamber and an outlet chamber separated by a deformable microporous membrane, the outlet chamber containing a perforated membrane support surface of concave compound curvature which is spaced from the wall of the outlet chamber, the deformable membrane being in contact with and conforming to the compound curvature of the support surface when fluid flows through the membrane from the inlet chamber to the outlet chamber.

4 Claims, 5 Drawing Figures

FILTER WITH INITIALLY FLAT MEMBRANE AND CURVED MEMBRANE SUPPORT

TECHNICAL FIELD

This invention relates to liquid filter devices of the type having a housing with an outlet separated from an inlet by a microporous membrane, and particularly to devices of this type wherein provision is made to assure that air or other gas accumulation on the membrane does not interfere with the flow of liquid through the membrane.

BACKGROUND ART

For the filtering of various kinds of liquids, the liquid is passed upwardly through a filter housing containing a flat, horizontal, microporous, hydrophilic membrane sealed to the walls of the filter housing and backed up by a flat grid or the like support. It is well known that when a hydrophilic membrane is wet (i.e when the pores are filled with the liquid being filtered), air or other gas cannot pass through the membrane except under increased pressure. Hence, if there is air or other gas in the liquid being filtered, it accumulates on the inlet surface of the membrane and blocks or interferes with the passage of liquid through the membrane. Further, once the membrane is wet, if there is air in the side of the housing underneath the membrane prior to commencing the filtration (as where the filter is periodically used at frequent intervals), the air can't escape except under a high pressure sufficient to drive it through the wet membrane, with threat of membrane rupture. It is well known to form or treat a portion of the membrane to render it hydrophobic so that the air or other gas can exit through such portion. For example, it is known to use a membrane with a hydrophilic central portion and a hydrophobic peripheral portion, or vice versa. But no matter the location of the hydrophobic portion or portions, the possibility remains that air or other gas can accumulate on the hydrophilic membrane portions. This possibility can be diminished by increasing the aggregate area of the hydrophobic portion or portions; however, this is disadvantageous in that what is ideal is that the maximum amount of membrane surface area be hydrophilic so that there is optimum liquid filtering efficiency.

Hence, there remains a need for a filter device, of the general type described, which provides optimum filtering efficiency while yet assuring against any accumulation of air or other gas on the inlet surface of the membrane.

DISCLOSURE OF THE INVENTION

As stated above, the membranes used in the filter devices of the type described are flat. The reason for this is that microporous membrane is manufactured as a flat sheet from which the individual membranes are cut. However, in the conception of the present invention it was recognized that microporous membrane currently on the market, while flat, nevertheless has sufficient inherent deformability, particularly when wet, that it can be deformed to compound curved configuration without threat of rupture. In the filter device of the present invention the membrane, which has the inherent deformability, is flat initially, i.e. prior to first use of the device for filtration, and has behind it a perforated membrane support surface of concave compound curvature which is spaced from the membrane. However, when the filter is first used, as to filter a liquid, the liquid being filtered wets the membrane and asserts pressure against the inlet surface of the membrane and thereby deforms the membrane against the curved membrane support, the membrane thereby assuming the compound curvature of the support. In the preferred embodiments the membrane has a hydrophobic center portion and when the filter device is in use, any air or other gas reaching the membrane inlet surface moves upwardly along the upwardly curved surface where it exits through the hydrophobic portion. Hence, there is assurance against any accumulation of air or other gas on the inlet surface of the membrane and yet with only a small portion of the membrane being hydrophobic.

Hence, the filter device of the present invention comprises a housing having an inlet chamber with a fluid inlet opening and an outlet chamber having a wall with a fluid outlet opening therein, a deformable microporous membrane separating these chambers and sealed to the housing, and a perforated membrane support surface of concave compound curvature in said upper chamber and spaced from the wall thereof, the membrane being initially flat and spaced from said membrane support surface but being in contact with and of the same compound curvature as that of said membrane support surface when the device is used.

In the preferred embodiment, the membrane support surface is formed by a plurality of circumferentially spaced, radially inwardly extending ribs in the outlet chamber, the surfaces of the ribs adjacent the membrane being of arcuate shape such that the combination of these spaced curved rib surfaces defines the peforated membrane support surface of concave compound curvature.

By the term "perforated surface" is meant a surface with openings therethrough irrespective of the shape of the openings or how formed.

BEST MODE FOR CARRYING OUT THE INVENTION

Figure 1:
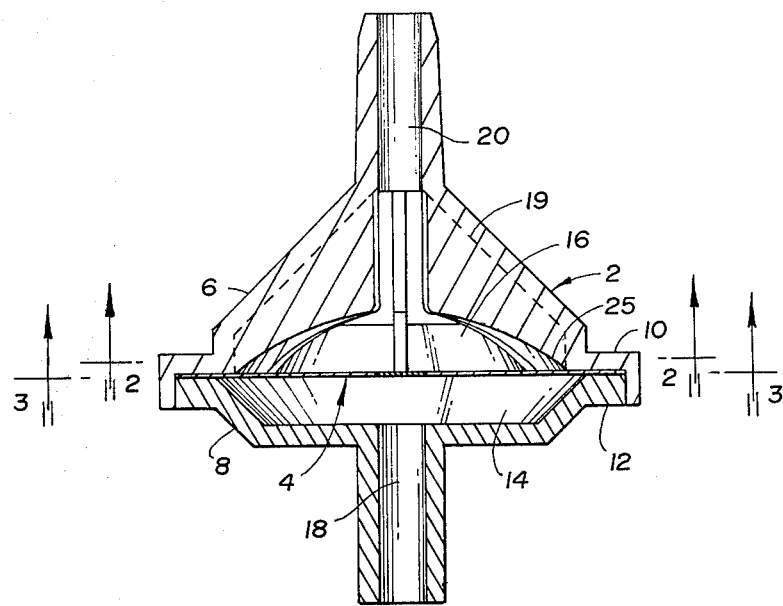
FIG. 1 shows a side view in section of a preferred embodiment of the invention.
Figure 2:
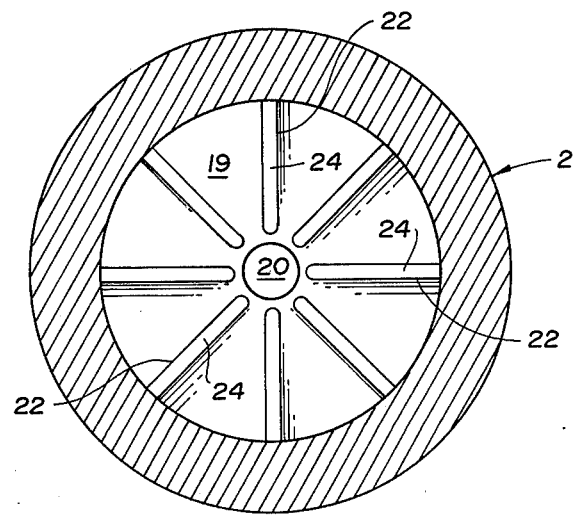
FIG. 2 shows a section taken on line 2—2 of FIG. 1.
Figure 3:
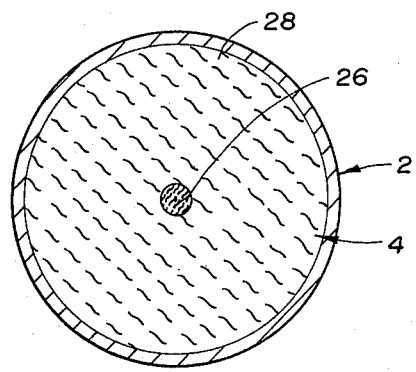
FIG. 3 shows a section taken on line 3—3 of FIG. 1 and shows a bottom view of the microporous membrane.

Referring now to FIGS. 1-3, the filter device comprises a housing 2 and a microporous membrane 4. The housing is made in the form of an upper molding 6 preferably of a clear thermoplastic, and a lower molding 8, also preferably of a clear thermoplastic, with radially outwardly extending flanges, 10 and 12 respectively, which are mated and sealed, with the round periphery of the membrane 4 therebetween. Hence, the membrane, sealed about its periphery within the housing, divides the housing into a lower inlet chamber 14 and an upper outlet chamber 16. The inlet chamber has a liquid inlet opening 18 for entrance of the liquid to be filtered, and the outlet chamber has a wall 19 with liquid outlet opening 20 for the filtrate.

Within the outlet chamber and spaced from the wall 19 thereof is an upwardly, concavely compound curved perforated membrane support surface which, in this preferred embodiment, is formed by a plurality of circumferentially spaced, radially inwardly extending ribs 22, the bottom surfaces 24 of which are of arcuate concave shape such that the combination of these spaced curved surfaces define the perforated support surface for the membrane. It should be noted that whereas the support surface is of concave compound curvature, its periphery 25 is in a plane substantially coplanar with the periphery of the membrane. In the preferred embodiment shown, the compound curvature of the membrane support surface, defined by the combination of the arcuate surfaces 24 of the ribs, is spherical, though other compound curvatures can be used if desired. Also, in this preferred embodiment, the ribs 22 are molded integrally with the upper molding 6, this being desirable to reduce manufacturing costs.

The membrane 4 has a round hydrophobic portion 26 at the center thereof, the remainder 28 of the membrane of this preferred embodiment being hydrophilic. Such a composite membrane can be made by bonding the hydrophobic portion to the hydrophilic portion. However, as is well known in the art, the simplest way to make a membrane which is for the most part hydrophilic but with a hydrophobic portion is to use a membrane which is hydrophilic but then coat the portion thereof desired to the hydrophobic with a material, such as a silicone oil, which renders such portion water repellant or hydrophobic. Hence, the simplest way to make the membrane 4 is to start with a hydrophilic membrane and then coat the central portion 26 thereof with a material such as silicone oil to render it hydrophobic. A silicone oil useful for this purpose is that currently manufactured and sold by the Dow Chemical Company of Midland, Mich. as a water repellant coating for fabrics and the like.

The membrane 4 is deformable, particularly when wet, the deformability being sufficient to allow it to be deformed to the compound curvature of the membrane support surface without rupture. Microporous hydrophilic membrane currently on the market has such deformability, an example being that marketed by Gelman Sciences, Inc. of Ann Arbor, Mich. under the trademark Tuffryn HT. This particular membrane is made of polysulfone and has a pore size of from about 0.2 microns though it will be understood that membrane of other material and/or pore sizes can be used if desired.

Figure 4:
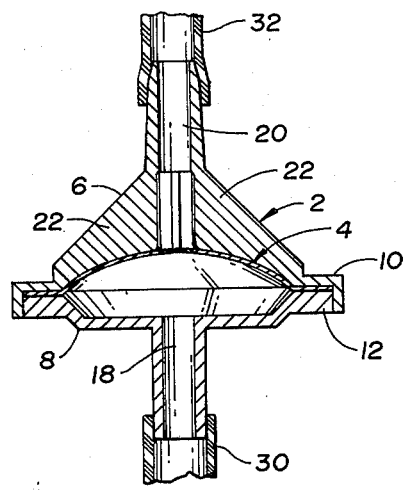
FIG. 4 is a view like that of FIG. 1, but while the filter device is in use causing the membrane to assume its curved configuration.

As shown in FIG. 1, in the filter device as manufactured and prior to use, the membrane is flat and is spaced from the membrane support surface (except at its periphery). However, as shown in FIG. 4, when the filter device is put into use to filter a liquid, the pressure differential between the lower and upper chambers caused by the pressure of the feed fluid flowing into the lower chamber and against the membrane causes the membrane to deform upwardly into contact with the membrane support whereupon the membrane assumes the upwardly concave curvature of the support surface. Hence, any air or other gas entering into the lower chamber from the connected feed fluid conduit 30, and also the air present in the lower chamber at the outset of the filtration, moves upwardly, or in a direction with an upward component, until it reaches the hydrophobic portion 26 of the membrane where it exits into the outlet chamber and then out through the outlet conduit 32 with the filtrate. The pressure differential necessary to cause the filtration can, of course, be created either by pulling a vacuum on the outlet of the filter device or by applying pressure to the feed liquid fed into the inlet.

Once the membrane is deformed to the compound curvature of the support surface, as aforesaid, it generally permanently remains of this curved configuration though if the membrane should withdraw from contact with the support when the device is out of use for a period, it is immediately pressed into contact with the support surface when use is resumed. It is within the purview of the invention to deform the membrane to its compound curved configuration as a final manufacturing step, as by wetting the membrane and applying pressure thereto to press the membrane into contact with the support; however, this adds additional expense and would simply be duplicative of the operation inherently performed the first time the filter device is used for filtration by the purchaser of the device.

Figure 5:
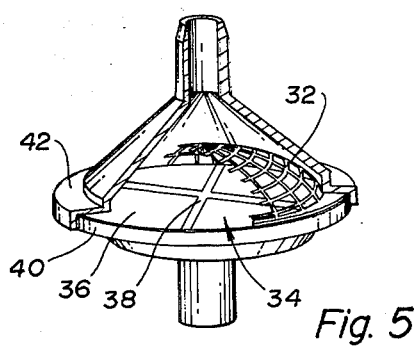
FIG. 5 is a perspective view, with parts broken away, of another embodiment of the invention.

The embodiment shown in FIG. 5 is the same as that of FIGS. 1–4 except in the following respects. In the FIG. 5 embodiment, the membrane support, instead of being in the form of the ribs of the preferred embodiment, is in the form of an upwardly concave grid member 32, the outer periphery of which is without the grid openings and overlays the periphery of the membrane 34 and, with the periphery of the membrane 34, is bonded and sealed between the flanges 40 and 42, respectively, of the lower and upper housing portions. Secondly, the membrane 34 of the FIG. 5 embodiment has a hydrophobic portion 38 in the form of a cross with the center of the cross being at the center of the membrane, the remainder of the membrane being in the form of quadrants 36 and being hydrophilic.

The concave grid member simply illustrates one of a number of alternative structures which can be used for the compound curved grid support surface and the membrane structure of the FIG. 5 embodiment illustrates the fact that any of various configurations can be used for the hydrophobic portion of the membrane. Indeed, it should be understood that whereas in the preferred embodiments the membrane includes a hydrophobic portion, ideally at least some of which is located centrally of the membrane, the practice of the invention in its broadest scope does not require the use of a membrane with both hydrophilic and hydrophobic portions. In some filtrations, for example, the amount of air or other gas in the liquid being filtered is so small that it is not necessary to cause its exit through the membrane but instead all that is required is to assure that the accumulation of the air or other gas does not greatly interfere with continued passage of the liquid through the membrane. With the present invention the air or other gas is caused to accumulate at the central portion of the membrane thereby leaving most of the membrane free of the gas and hence free to allow passage of the liquid therethrough. The cardinal feature of the present invention, in its broadest scope, is that it provides a filter device with a supported membrane which is curved to spherical or other compound curvature and yet which can be manufactured at low cost, this by reason of the use of a membrane which is initially flat and which can therefore be cut from inexpensively manufactured flat membrane sheet stock.

Hence, it will be understood that while the invention has been described in its particulars with respect to preferred embodiments thereof, various changes and modifications may be made all within the full and intended scope of the claims which follow.

What is claimed is:

1. A filter device comprising a housing having an inlet chamber with a fluid inlet opening and an outlet chamber with a wall having a fluid outlet opening, a deformable filter membrane separating said chambers and sealed to said housing, said outlet chamber containing a perforated membrane support surface of concave compound curvature spaced from the wall of the outlet chamber, said membrane being held by said housing so as to be initially flat and spaced from said support surface, said membrane being sufficiently deformable so as to be forced into contact with and conform to the compound curvature of said support surface under normal transmembrane pressure when fluid flows through the membrane from said inlet chamber to said outlet chamber.

2. A filter device as set forth in claim 1 wherein said membrane is for the most part hydrophilic but has a hydrophobic portion at least some of which is adjacent the center of the membrane.

3. A filter device as set forth in claim 1 wherein said membrane support is formed by a plurality of circumferentially spaced, radially inwardly extending ribs which are integral with said housing and which have arcuate bottom surfaces the combination of which defines the perforated support surface of concave compound curvature.

4. A filter device as set forth in claim 1 wherein said membrane is formed into permanent contact with and conforming to said compound curvature of said support.

* * * * *